(12) United States Patent
Gdaniec

(10) Patent No.: US 11,090,211 B2
(45) Date of Patent: Aug. 17, 2021

(54) HEAT CONTROL DEVICE FOR AN INCUBATOR FOR INFANTS, INCUBATOR AND METHOD FOR THE HEAT CONTROL OF AN INCUBATOR

(71) Applicant: Drägerwerk AG & Co. KGaA, Lübeck (DE)

(72) Inventor: Przemyslaw Gdaniec, Hamburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 122 days.

(21) Appl. No.: 16/395,564

(22) Filed: Apr. 26, 2019

(65) Prior Publication Data

US 2019/0247259 A1 Aug. 15, 2019

Related U.S. Application Data

(63) Continuation of application No. 14/948,963, filed on Nov. 23, 2015, now Pat. No. 10,314,756.

(30) Foreign Application Priority Data

Nov. 27, 2014 (DE) .................. 10 2014 017495.6

(51) Int. Cl.
*A61G 11/00* (2006.01)
*A61F 7/00* (2006.01)

(52) U.S. Cl.
CPC ............ *A61G 11/00* (2013.01); *A61F 7/0053* (2013.01); *A61F 7/0085* (2013.01); *A61F 2007/006* (2013.01); *A61F 2007/0072* (2013.01); *A61F 2007/0086* (2013.01); *A61F 2007/0088* (2013.01); *A61F 2007/0093* (2013.01); *A61G 11/007* (2013.01); *A61G 2200/14* (2013.01); *A61G 2203/46* (2013.01)

(58) Field of Classification Search
CPC .. A61G 11/00; A61G 11/007; A61G 2200/14; A61G 2203/46
See application file for complete search history.

(56) References Cited

U.S. PATENT DOCUMENTS

| 6,063,020 | A | * | 5/2000 | Jones | ..................... | A61G 11/00 600/22 |
| 10,314,756 | B2 | * | 6/2019 | Gdaniec | ................ | A61G 11/00 |
| 2004/0234254 | A1 | * | 11/2004 | Czupich | ................ | A61G 11/00 392/403 |

* cited by examiner

*Primary Examiner* — Christine H Matthews
(74) *Attorney, Agent, or Firm* — McGlew and Tuttle, P.C.

(57) ABSTRACT

An infant incubator heat control device includes a temperature-detecting device providing chamber interior and incubator heater temperature measured values. A first mode of operation has an interior temperature set value, a temperature of the heater set value is calculated as a function of the interior temperature set value and of the chamber interior temperature measured value. A controlled variable is calculated for the heater as a function of the temperature of the heater set value and of the heater measured value. A second mode of operation calculates a temperature of the heater set value independently of the chamber interior temperature measured value. A controlled variable is calculated for the heater as a function of the set value for the temperature of the heater and of the heater temperature measured value.

17 Claims, 2 Drawing Sheets

HEAT CONTROL DEVICE FOR AN INCUBATOR FOR INFANTS, INCUBATOR AND METHOD FOR THE HEAT CONTROL OF AN INCUBATOR

CROSS REFERENCE TO RELATED APPLICATIONS

This application is a continuation application and claims the benefit of priority under 35 U.S.C. § 120 of U.S. patent application Ser. No. 14/948,963 filed Nov. 23, 2015, which claims the benefit of priority under 35 U.S.C. § 119 of German Patent Application DE 10 2014 017 495.6 filed Nov. 27, 2014, the entire contents of each application are incorporated herein by reference.

FIELD OF THE INVENTION

The present invention pertains to a heat control device for an incubator for infants, an incubator and a method for the heat control of an incubator.

BACKGROUND OF THE INVENTION

Incubators for infants are known which have an incubator chamber, into which the infant is placed, wherein the incubator chamber has a hood that can assume a closed position, in which the incubator chamber is extensively thermally insulated against the surrounding area, or an open position, in which the incubator chamber is in contact with the surrounding area. Contact with the infant by the parents or health care staff is facilitated in the open position. After changing from the open position into the closed position, it is important to bring the air temperature in the incubator chamber quickly to the desired temperature.

SUMMARY OF THE INVENTION

An object of the present invention is to provide a heat control device (infant incubator heat controller or infant incubator heat control system) for an incubator, which makes possible a fast setting of the desired temperature, as well as a corresponding incubator and a corresponding method for the heat control of an incubator.

A heat control device according to the present invention for an incubator for infants comprises a temperature-detecting device for detecting at least one first temperature measured value of a temperature in the interior of an incubator chamber and at least one second temperature measured value of a temperature of a heater of the incubator. The heat control device has a first mode of operation and a second mode of operation. In the first mode of operation, a cascade control is provided, wherein a set value is preset for the temperature in the interior of the incubator chamber, a set value is calculated in a first control step for the temperature of the heater as a function of the set value for the temperature in the interior of the incubator chamber and of the at least one first temperature measured value and a controlled variable is calculated in a second control step for the heater as a function of the set value for the temperature of the heater and of the at least one second temperature measured value. In the second mode of operation, a set value is calculated in a first control step for the temperature of the heater independently of the at least one first temperature measured value and a controlled variable is calculated in a second control step for the heater as a function of the set value for the temperature of the heater and of the at least one second temperature measured value.

A control of the heater in two different modes of operation is made possible in this way. Since the second mode of operation is independent of the first temperature measured value of a temperature in the interior of the incubator chamber, this mode of operation is suitable for the operation with an open incubator chamber, resulting in a fast and accurate setting of a temperature of the heater in the open state of the incubator. The first mode of operation is, on the other hand, suitable for the operation with closed incubator chamber. The two modes of operation can readily be implemented together due to the cascade control.

The heat control device preferably makes possible a control of the body temperature of the infant, wherein the temperature-detecting device is designed for detecting a measured value of the body temperature of the infant and for detecting a measured value of an air temperature in the interior of the incubator chamber as first temperature measured values. The first control step of the first mode of operation comprises a cascade control, wherein the set value for the temperature in the interior of the incubator chamber is a set value for the body temperature of the infant and a set value is calculated in a first cascade step of the first control step for the air temperature in the interior of the incubator chamber as a function of the set value for the body temperature of the infant and of the measured value of the body temperature of the infant. A set value is calculated in a second cascade step of the first control step for the temperature of the heater as a function of the set value for the air temperature in the interior of the incubator chamber and of the measured value of the air temperature in the interior of the incubator chamber.

In the heat control device the temperature-detecting device may designed for detecting a measured value of the air temperature in the interior of the heater and for detecting a measured value of a temperature of a heating element as second temperature measured values, and the second control step of the first and/or second mode of operation comprises a cascade control, wherein the set value for the temperature of the heater is a set value for the air temperature in the interior of the heater and a set value is calculated in a first cascade step of the second control step for the temperature of the heating element as a function of the set value for the air temperature in the interior of the heater and of the measured value of the air temperature in the interior of the heater. The controlled variable for the heater is calculated in a second cascade step of the second control step as a function of the set value for the temperature of the heating element and of the measured value of the temperature of the heating element.

An advantageous calculation of the set value for the temperature of the heater is made possible by a heat control device, in which the temperature-detecting device is designed for detecting a measured value of the ambient temperature of the incubator and wherein a set value is preset in the second mode of operation for the temperature in the interior of the incubator chamber, wherein the set value is calculated in the first control step of the second mode of operation for the temperature of the heater as a function of the set value for the temperature in the interior of the incubator chamber and of the measured value of the ambient temperature.

The heat control device may be designed to control a blower of the heater, wherein a minimum air flow through the heater is set in the second mode of operation in order to ensure a heat exchange within the heater. An optimal function of the control in the second mode of operation is ensured in this way.

Furthermore, an incubator status-detecting device may be provided, which detects an open state or a closed state of the incubator chamber and wherein the heat control device operates the heater in the closed state in the first mode of operation and in the open state in the second mode of operation.

An incubator for infants according to the present invention comprises an incubator chamber for accommodating the infant, which is in contact with the surrounding area in an open state and which is at least partially thermally insulated against the surrounding area in a closed state; an incubator status sensor for detecting whether the incubator chamber is in the open or closed state; and a heater for heating the air in the incubator chamber, which has an air inflow sensor, which detects an air temperature of the air flowing from the heater into the incubator chamber, wherein the heater is designed to be controlled such that the air temperature measured by the air inflow sensor of the air flowing from the heater into the incubator chamber corresponds to a preset set value, when the incubator status sensor detects that the incubator chamber is in the open state. In this way, the heater can be automatically controlled in the open state to a set value of the air temperature of the air flowing from the heater into the incubator chamber. Thus, an effective and accurate preheating of the heater is made possible in the open state, as a result of which fast heating of the air in the interior of the incubator chamber is made possible upon a return into the closed state.

The present invention provides, furthermore, an incubator for infants, particularly an incubator as described above with a heat control device as described above.

A method according to the present invention for the heat control of an incubator for infants comprises the method steps of detecting an open or closed state of an incubator chamber and selecting a first or second mode of operation of a cascade control as a function of the state of the incubator chamber, wherein a heater is operated in the first mode of operation in the closed state and in the second mode of operation in the open state. In the first mode of operation, a cascade control is provided, a set value is calculated in a first control step for the temperature of the heater as a function of the set value for the temperature in the interior of the incubator chamber and of at least one first temperature measured value of the temperature in the interior of the incubator chamber and a controlled variable is calculated in a second control step for the heater as a function of the set value for the temperature of the heater and of at least one second temperature measured value. In the second mode of operation, a set value is calculated in a first control step for the temperature of the heater independently of a temperature in the interior of the incubator chamber and a controlled variable is calculated in a second control step for the heater as a function of the set value for the temperature of the heater and of the at least one second temperature measured value.

The method makes possible a heat control of an incubator with the advantages mentioned above.

Further advantages and features of the present invention appear from the following description and from the drawings to which reference is made. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
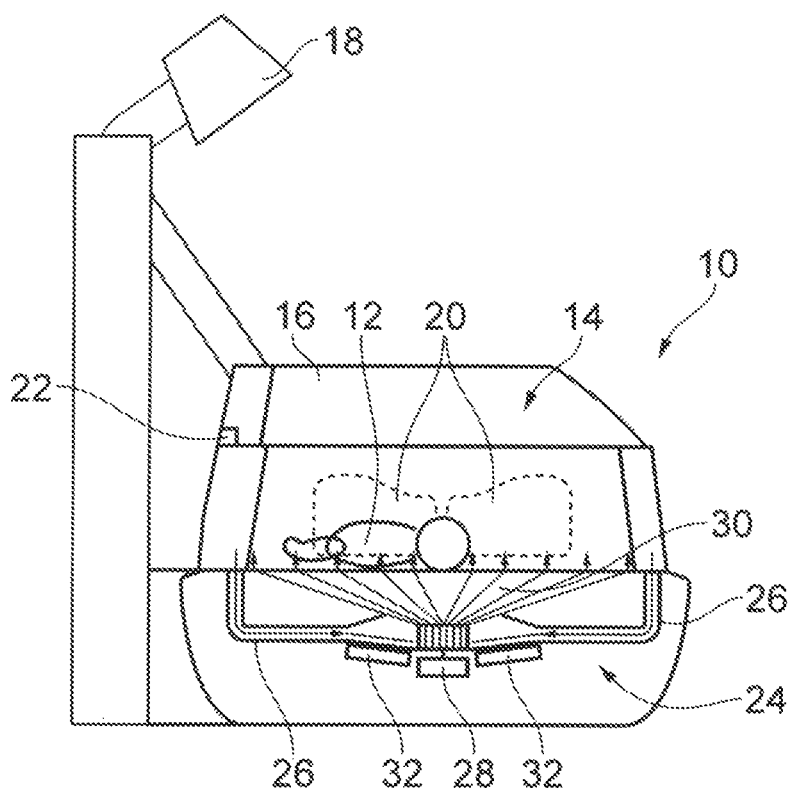
FIG. 1 is a view of an incubator according to the present invention in a closed state.
Figure 2:
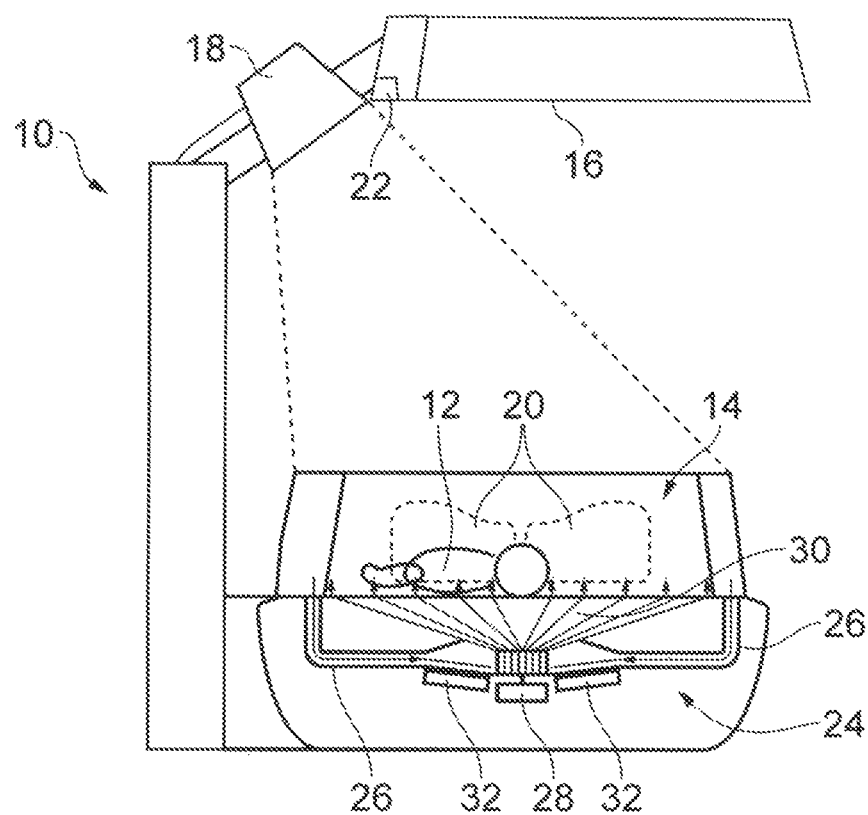
FIG. 2 is a view of the incubator from FIG. 1 in an open state.

Referring to the drawings, FIGS. 1 and 2 show an incubator 10 for an infant 12 with an incubator chamber 14 for accommodating the infant 12.

The incubator 10 comprises a hood 16, which forms the upper area of the incubator chamber 14. The hood 16 is shown in FIG. 1 in a closed state, in which the incubator chamber 14 is essentially thermally insulated against the surrounding area. The hood 16 can be brought from the closed position into an open position, which is shown in FIG. 2. In the open position, the infant can be placed into the incubator chamber 14 and a contact between the infant and parents or health care staff is facilitated. In the open position, the incubator chamber 14 is in direct contact with the surrounding area.

A heat lamp 18 is provided, which makes possible a thermal radiation of the incubator chamber 14 and of the infant in the open position of the hood 16.

The incubator chamber 14 has, furthermore, side windows 20, through which it is possible to reach into the interior of the incubator chamber 14 even in the closed state of the incubator chamber 14.

An incubator status sensor 22 for detecting whether the incubator chamber is in the open or closed state is provided.

Figure 3:
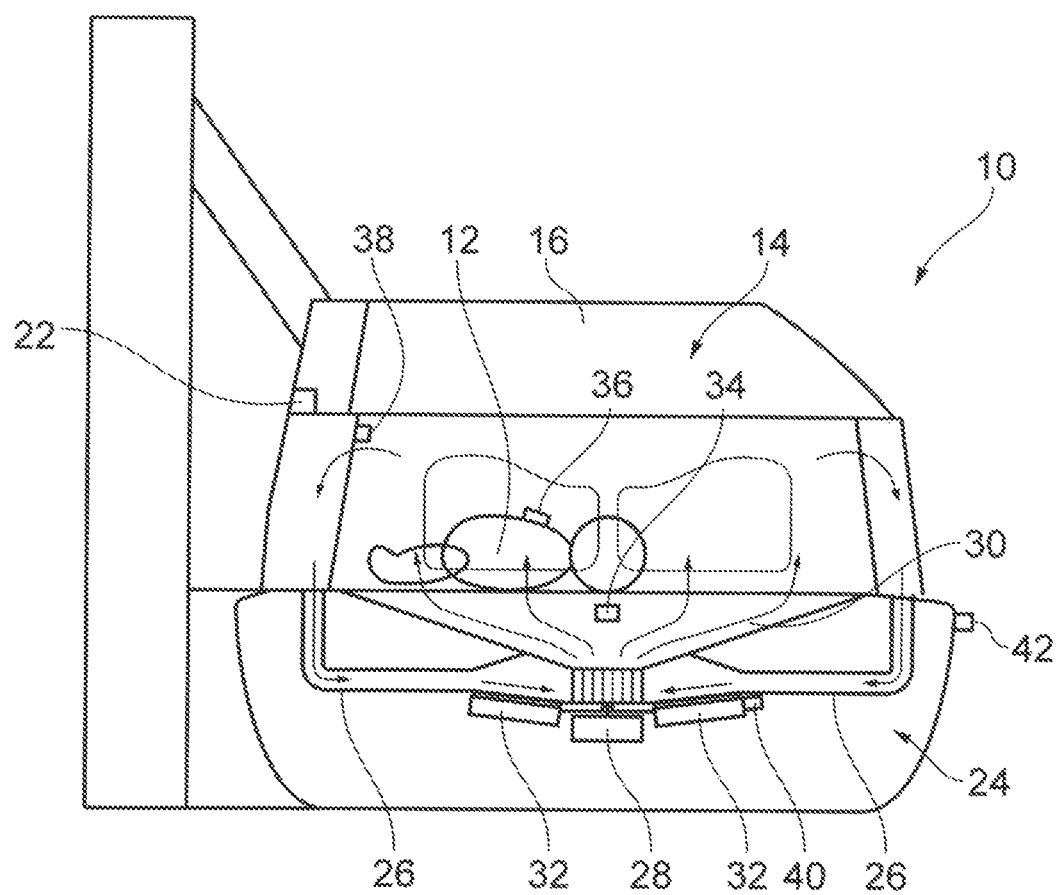
FIG. 3 is a detail view of the incubator from FIG. 2 with a heat control device according to the present invention.

FIG. 3 shows a detail view of the incubator chamber 14 and a heater 24. The heater 24 is intended for heating the air in the incubator chamber 14. The heater 24 comprises an air intake duct 26, which leads from the head and foot ends of the incubator chamber 14 to a blower 28. From the blower 28, an air supply duct 30 leads to the longitudinal sides of the incubator chamber 14 on which sides are provided discharge openings, via which the air heated in the heater 24 flows into the incubator chamber 14.

In the air intake duct 26 and/or in the air supply duct 30 is provided a heating element 32, which discharges heat to the air being guided in the ducts and heats this air. In the embodiment being shown, the heating element is designed as a plate, on which the air flow is guided along. Electric heating rods which are connected to the plate in a heat-conducting manner are provided on the underside of the plate.

However, a different geometric arrangement of the air ducts 26, 30, of the blower 28 and of the heating element 32 may also be provided. For example, a plurality of heating elements 28 may also be provided, which can be controlled individually or together.

The heater 24 has, in addition, an air inflow sensor 34, which detects an air temperature of the air flowing from the heater 24 into the incubator chamber 14. In the embodiment being shown, the air inflow sensor 34 is arranged in the air supply duct 30, preferably in the vicinity of the discharge openings. A plurality of air inflow sensors 34 may also be arranged at various areas, as a result of which, for example, the temperature distribution can be checked for uniformity.

The heater 24 is designed to be controlled in the open state of the hood 16, so that the temperature of the air flowing from the heater 24 into the incubator chamber 14, which temperature is measured by the air inflow sensor 34, corresponds to a preset set value. The status of the hood 16 is automatically detected by the incubator status sensor 22. In this way, the heater 24 in the open state of the incubator chamber 14 can automatically be controlled to a set value of the air temperature of the air flowing from the heater 24 into the incubator chamber 14. Thus, an effective and accurate preheating of the heater 24 in the open state is made possible, as a result of which fast heating of the air in the interior of the incubator chamber 14 is made possible upon a return into the closed state.

The incubator 10 has, furthermore, a body temperature sensor 36 at the body of the infant 12, which detects a body temperature (skin temperature) of the infant 12; an inside temperature sensor 38, which detects an air temperature in the interior of the incubator chamber 14; a heating element temperature sensor 40, which detects a temperature of the heating elements 32; and an outside temperature sensor 42, which detects a temperature of the surrounding area of the incubator.

The incubator status sensor 22, the air inflow sensor 34, the body temperature sensor 36, the inside temperature sensor 38, the heating element temperature sensor 40 and the outside temperature sensor 42 are connected to a heat control device 44 of the heater 24.

Figure 4:
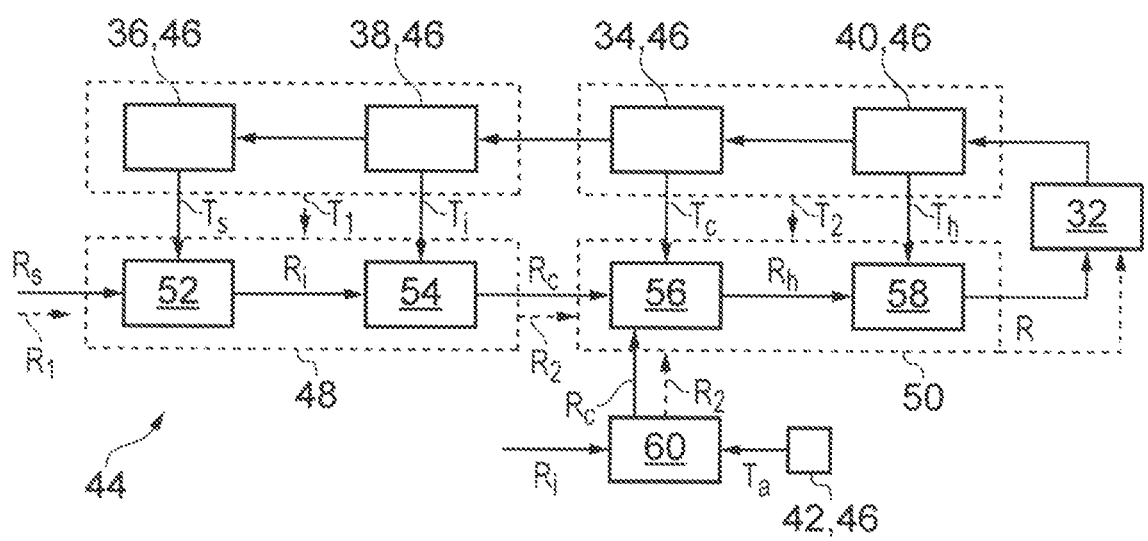
FIG. 4 is a schematic view of a heat control device according to the present invention.

FIG. 4 shows a schematic view of the heat control device 44.

The basic principle of the heat control device 44 is first explained based on the control elements illustrated with dotted lines in FIG. 4.

The heat control device 44 comprises a temperature-detecting device 46 for detecting at least one first temperature measured value T1 of a temperature in the interior of an incubator chamber and at least one second temperature measured value T2 of a temperature of a heater of the incubator.

In the embodiment being shown, a first temperature measured value T1 may be a measured value Ts of the body temperature of the infant and/or a measured value Ti of the air temperature in the interior of the incubator chamber 14.

A second temperature measured value T2 may be a measured value Tc of the air temperature in the interior of the heater 24 and/or a measured value Th of the temperature of the heating element 32.

The temperature-detecting device 46 may be formed by the corresponding sensors, i.e., the air inflow sensor 34, the body temperature sensor 36, the inside temperature sensor 38 and the heating element temperature sensor 40 and/or by an interface for corresponding external sensors.

The heat control device 44 has a first mode of operation and a second mode of operation.

A cascade control is provided in the first mode of operation. A set value R1 is preset for the temperature in the interior of the incubator chamber.

A set value R2 is calculated in a first control step 48 for the temperature of the heater as a function of the set value R1 for the temperature in the interior of the incubator chamber and of the at least one first temperature measured value T1.

The calculated set value R2 is forwarded to a second control step 50 of the cascade control, in which a controlled variable R is calculated for the heater 24 as a function of the set value R2 for the temperature of the heater and of the at least one second temperature measured value T2.

In this way, a cascade control with two stages is provided, wherein the first stage forms a control of the temperature within the incubator chamber 14 and the second stage forms a control of the temperature within the heater. The cascade control makes possible a fast control, wherein specific temperature limits are provided for each control stage. For example, a maximum temperature of 39° C. is provided for the air temperature in the interior of the incubator chamber 14 in order to prevent an overheating of the infant. On the other hand, for example, a maximum temperature of 200° C., preferably 150° C., is provided in the interior of the heater 24.

Each control step is carried out in this case such that a deviation between the set value and the measured value is minimized.

The first mode of operation is suitable for the closed state of the incubator chamber 14 because a stable temperature within the incubator chamber 14 thermally insulated from the surrounding area becomes established in this state. Disturbances, for example, by opening one of the side windows 20, may be quickly compensated by the control in the first mode of operation.

Subsequently, a concrete embodiment with a four-stage cascade control is described, which is shown by solid lines in FIG. 4 and in which the two control steps 48, 50 mentioned above are each divided into two-stage cascade controls.

For this purpose, the temperature-detecting device is designed for detecting the measured value Ts of the body temperature of the infant 12, the measured value Ti of the air temperature in the interior of the incubator chamber 14, the measured value Tc of the air temperature in the interior of the heater 24 and the measured value Th of the temperature of the heating element 32.

The set value R1 for the temperature in the interior of the incubator chamber 14 is a set value Rs for the body temperature of the infant. The body temperature of the infant is controlled in this way.

A set value Ri is calculated in a first cascade step 52 of the first control step 48 for the air temperature in the interior of the incubator chamber 14 as a function of the set value Rs for the body temperature of the infant 12 and of the measured value Ts of the body temperature of the infant 12.

A set value Rc is calculated in a second cascade step 54 of the first control step 48 for the air temperature in the interior of the heater 24 as a set value R2 for the temperature of the heater 24. The set value Rc for the air temperature in the interior of the heater 24 is calculated as a function of the set value Ri for the air temperature in the interior of the incubator chamber and of the measured value Ti of the air temperature in the interior of the incubator chamber.

A set value Rh is calculated in a first cascade step 56 of the second control step 50 for the temperature of the heating element 32 as a function of the set value Rc for the air temperature in the interior of the heater 24 and of the measured value Tc of the air temperature in the interior of the heater 24.

The controlled variable R for the heater 24 is calculated in a second cascade step 58 of the second control step 50 as a function of the set value Rh for the temperature of the heating element and of the measured value Th of the temperature of the heating element.

The controlled variable R for the heater 24 is, for example, a current value for the electric heating rods of the heating element 32.

Since biological processes play a large role in the control of the body temperature of the infant 12, on the one hand, correspondingly strong non-linear effects in the control may be taken into consideration there. Furthermore, strong disturbances in the temperature in the interior of the incubator chamber 14, for example, due to the opening of the side windows 20 to reach into the incubator chamber, may be taken into consideration. On the other hand, rather simple linear ratios and slight disturbances may be expected for the control steps of the temperature in the interior of the heater 24 and of the temperature of the heating element 32. The individual control steps can each be adapted by the cascade control corresponding to the circumstances.

Furthermore, it is relatively simple to incorporate a second mode of operation into the cascade control as described below.

A set value R2 is calculated in a first control step 60 in the second mode of operation for the temperature of the heater 24 and a set value Rc is calculated for the air temperature in the interior of the heater 24 independently of the at least one first temperature measured value T2 and independently of the measured value Ts for the body temperature of the infant and independently of the measured value Ti of the air temperature in the interior of the incubator chamber.

Analogously to the first mode of operation, a controlled variable is calculated in a second control step 50 according to the second mode of operation for the heater 24 as a function of the set value R2 for the temperature of the heater 24 and of the at least one second temperature measured value T2.

Because the second control step 50 in the second mode of operation is carried out analogously to the first mode of operation, the two modes of operation may be combined into a common control device. Since the second mode of operation is independent of the first temperature measured value of a temperature in the interior of the incubator chamber, this mode of operation is suitable for the operation with open incubator chamber, resulting in a fast and accurate setting of a temperature of the heater in the open state of the incubator.

In the embodiment being shown, the set value R2 for the temperature of the heater 24 and the set value Rc for the air temperature in the interior of the heater 24 are calculated as a function of a preset set value Ri for the temperature in the interior of the incubator chamber 14 and a measured value Ta of the ambient temperature. For this purpose, the temperature-detecting device 46 is designed for detecting the measured value Ta of the ambient temperature of the incubator 10. The measured value Ta of the ambient temperature is detected by the outside temperature sensor in the embodiment being shown in FIG. 3.

The ambient temperature may be considered to be the lowest possible temperature which can be reached in the control, since generally no cooling is provided for incubators. The temperature difference ratio (Tc−Ta)/(Ti−Ta) is constant in the stationary case and almost constant in the dynamic case in case of similar dynamics of Tc and Ti:

$$(T_c - T_a)/(T_i - T_a) = k \quad (1)$$

wherein k is a constant.

A set value Rc can thus be calculated for the air temperature in the interior of the heater 24 from this ratio due to the presetting of a set value Ri for the temperature in the interior of the incubator chamber 14.

As an alternative or in addition, the set value Rc can be calculated for the air temperature in the interior of the heater 24 and the set value R2 can be calculated for the temperature of the heater 24 from the radiation output $P_{IR}$ of the heat lamp 18.

In the open sate of the incubator chamber 14, in so-called open care, the infant 12 has a specific heat demand depending on state of health and clothing. The heat lamp 18 increases the body temperature Ts against the ambient temperature Ta in proportion to the output $P_{IR}$. Thus, $$T_s = P_{IR} k_{I2s} + T_a \quad (2).$$

In the closed state, in so-called closed care, the air temperature Ti shall correspond approximately to the desired body temperature Ts. The temperature Tc needed later in the interior of the heater 24 can then be calculated later from the temperature ratio mentioned above:

$$T_c = (T_i - T_a)k + T_a \quad (3)$$

wherein, with the above-mentioned assumption that Ti equals Ts, it is possible to obtain:

$$T_c = (T_s - T_a)k + T_a \quad (4)$$

and by inserting equation (2):

$$T_c = (P_{IR} k_{I2s})k + T_a \quad (5).$$

Thus, the desired temperature Rc in open care can be calculated with $$R_c = (P_{IR} k_{I2s})k + T_a \quad (6)$$

as a function of the radiation output $P_{IR}$ of the heat lamp 18 and of the ambient temperature.

In this way, the heater 24 can be operated in the open state of the incubator as a function of the measured ambient temperature and preferably radiation output $P_{IR}$ of the heat lamp 18 and of the body temperature Ts of the infant 12 in a way that would correspond to a desired air temperature in the incubator chamber 14 in the closed state. In this way, a preheating of the heater 24, i.e., of the heating elements 32 and the air ducts 26, 30, takes place so that a fast and reliable setting of the desired temperature is made possible in case of a change from the open state into the closed state due to the control cascade.

The second mode of operation can be applied in a combined manner both with a manual mode of the heat lamp 18, in which the physician himself sets the heat output, and with a controlled mode in which the radiation output $P_{IR}$ is controlled as a function of the body temperature Ts of the infant.

In the second mode of operation in the embodiment variant being described, the set value Rc, representing the set value R2 for the temperature of the heater 24, is calculated for the air temperature in the interior of the heater 24 independently of the first temperature measured value (T1), which is provided in the first mode of operation for the calculation of the set value R2 for the temperature of the heater 24, i.e., the measured value (Ti) of the air temperature in the interior of the incubator chamber (14).

The blower 28 of the heater 24 is controlled in this case by the heat control device 44, wherein a minimum air flow through the heater 24 is set in the second mode of operation in order to ensure a heat exchange within the heater 24 between the heating element 32 and the air duct walls and the corresponding temperature sensors.

In the embodiment being shown, the heat control device 44 has, furthermore, an incubator status-detecting device, which is embodied, for example, by the incubator status sensor 22 or a corresponding interface for an external sensor.

The incubator status-detecting device detects the open state or the closed state of the incubator chamber 14. Depending on the detected state of the incubator chamber 14, the heat control device 44 will operate the heater 24 in the closed state in the first mode of operation and in the open state in the second mode of operation. In this way, an automatic adaptation of the mode of operation takes place.

While specific embodiments of the invention have been shown and described in detail to illustrate the application of the principles of the invention, it will be understood that the invention may be embodied otherwise without departing from such principles.

APPENDIX:

List of Reference Numbers

10 Incubator
12 Infant
14 Incubator chamber
16 Hood
18 Heat lamp
20 Window
22 Incubator status sensor
24 Heater
26 Air intake duct
28 Blower
30 Air supply duct
32 Heating element
34 Air inflow sensor
36 Body temperature sensor
38 Inside temperature sensor
40 Heating element temperature sensor
42 Outside temperature sensor
44 Heat control device
46 Temperature-detecting device
48 First control step
50 Second control step
52 Cascade step
54 Cascade step
56 Cascade step
58 Cascade step
60 First control step

What is claimed is:

1. An infant incubator heat control device comprising:
a temperature-detecting device detecting at least one first temperature measured value of a temperature in an interior of an incubator chamber for accommodating an infant and detecting at least one second temperature measured value of a temperature of a heater of an incubator;
a control device configured to perform a first mode control and a second mode control, the first mode control comprising:
a first mode first control step calculating a heater temperature calculated set value as a function of a preset interior set value for the temperature in the interior of the incubator chamber and as a function of the at least one first temperature measured value;
a first mode second control step calculating a controlled variable for the heater as a function of the heater temperature calculated set value and as a function of the at least second temperature measured value, the second mode control providing a second mode of operation comprising:
a second mode first control step calculating a set value for the temperature of the heater independently of the at least one first temperature measured value; and
a second mode second control step calculating a controlled variable for the heater as a function of the set value for the temperature of the heater and as a function of the at least one second temperature measured value.

2. An infant incubator heat control device in accordance with claim 1, wherein:
the at least one first temperature measured value comprises a measured value of a body temperature of the infant and a measured value of the temperature in the interior of the incubator chamber;
the set value for the temperature in the interior of the incubator chamber is a set value for the body temperature of the infant, for the first mode first control step; and
the first mode first control step comprises:
a first cascade step comprising calculating a set value for the air temperature in the interior of the incubator chamber as a function of the set value for the body temperature of the infant and as a function of the measured value of the body temperature of the infant; and
a second cascade step comprising calculating the heater temperature calculated set value as a function of the set value for the air temperature in the interior of the incubator chamber and as a function of the measured value of the air temperature in the interior of the incubator chamber.

3. An infant incubator heat control device in accordance with claim 1, wherein:
the temperature-detecting device is configured to detect a measured value of an air temperature in an interior of the heater and to detect a measured value of a temperature of a heating element as second temperature measured values;
the set value for the temperature of the heater is a set value for the air temperature in the interior of the heater; and
the first mode second control step and the second mode second control step each comprise:
a first cascade step calculating a set value for the temperature of the heating element as a function of the set value for the air temperature in the interior of the heater and as a function of the measured value of the air temperature in the interior of the heater; and
a second cascade step calculating the controlled variable for the heater as a function of the set value for the temperature of the heating element and as a function of the measured value of the temperature of the heating element.

4. An infant incubator heat control device in accordance with claim 1, wherein:
the temperature-detecting device is configured to detect a measured value of ambient temperature of the incubator;
the second mode control is based on a preset set value for the temperature in the interior of the incubator chamber; and
the second mode second control step calculates the set value for the temperature of the heater as a function of the set value for the temperature in the interior of the incubator chamber and as a function of the measured value of the ambient temperature.

5. An infant incubator heat control device in accordance with claim 1, wherein the controlled variable for the heater controls a blower of the heater, wherein in the second mode of operation a minimum air flow through the heater is set to ensure a heat exchange within the heater.

6. An infant incubator heat control device in accordance with claim 1, further comprising:
an incubator status-detecting device configured to detect an open state or a closed state of the incubator chamber; and
in the closed state the heat control device operates the heater in the first mode of operation; and
in the open state the heat control device operates the heater in the second mode of operation.

7. An infant incubator heat control device in accordance with claim 1, further comprising:
an air inflow sensor arranged in an air supply duct of the heater, wherein the air inflow sensor detects an air temperature of air flowing from the heater into the incubator chamber.

8. An infant incubator heat control device in accordance with claim 7, wherein the air inflow sensor is arranged in an area of discharge openings of the heater, the discharge openings being in fluid communication with the incubator chamber.

9. An infant incubator heat control device in accordance with claim 1, wherein the control device comprises electronics.

10. An infant incubator comprising:
an incubator chamber for accommodating an infant, the incubator chamber being in contact with a surrounding area in an open state and the incubator chamber being at least partially thermally insulated against the surrounding area in a closed state;
an incubator status-detecting device configured to detect the open state or the closed state of the incubator chamber;
a heater for heating the air in the incubator chamber, the heater comprising an air inflow sensor, which detects an air temperature of the air flowing from the heater into the incubator chamber, the air inflow sensor being arranged between the heater and discharge openings for delivering the air to the incubator chamber; and
an infant incubator heat control device configured to control the heater such that the air temperature, measured by the air inflow sensor of the air flowing from the heater into the incubator chamber corresponds to a preset set value, when the incubator status-detecting be device detects that the incubator chamber is in the open state.

11. An infant incubator in accordance with claim 10, wherein the infant incubator heat control device comprises:
a temperature-detecting device detecting at least one first temperature measured value of a temperature in an interior of the incubator chamber and detecting at least one second temperature measured value of a temperature of the heater of the incubator;
a first mode control providing a first mode of operation comprising a cascade control comprising:
a first mode first control step calculating a heater temperature calculated set value as a function of a preset interior set value for a temperature in the interior of the incubator chamber and as a function of the at least one first temperature measured value;
a first mode second control step calculating a controlled variable for the heater as a function of the heater temperature calculated set value and as a function of the at least one second temperature measured value; and a second mode control providing a second mode of operation comprising:
a second mode first control step calculating a set value for the temperature of the heater independently of the at least one first temperature measured value; and
a second mode second control step calculating a controlled variable for the heater as a function of the set value for the temperature of the heater and as a function of the at least one second temperature measured value.

12. An infant incubator in accordance with claim 10, wherein the air inflow sensor is arranged in an area of the discharge openings of the heater, the discharge openings being in fluid communication with the incubator chamber, the discharge openings defining at least a portion of a fluid flow path for delivering the air to the incubator chamber, at least a portion of the air inflow sensor being arranged in the fluid flow path.

13. An infant incubator in accordance with claim 10, wherein the infant incubator heat control device comprises electronics.

14. A method for a heat control of an incubator for infants, the method comprising:
detecting an open state or closed state of an incubator chamber of an incubator for an infant;
performing a cascade control first mode of operation or second mode of operation via a control device as a function of the open state or closed state of the incubator chamber, wherein a heater of the incubator is operated in the first mode of operation in the closed state and in the second mode of operation in the open state;
detecting with a temperature-detecting device at least one first temperature measured value of a temperature in an interior of the incubator chamber and detecting at least one second temperature measured value of a temperature of the heater of the incubator, wherein the first mode of operation comprises:
a first mode first control step calculating a heater temperature calculated set value as a function of a preset interior set value for a temperature in the interior of the incubator chamber and as a function of the at least one first temperature measured value;
a first mode second control step calculating a controlled variable for the heater as a function of the heater temperature calculated set value and as a function of the at least one second temperature measured value; and
the second mode of operation comprises:
a second mode first control step calculating a set value for the temperature of the heater independently of the at least one first temperature measured value; and
a second mode second control step calculating a controlled variable for the heater as a function of the set value for the temperature of the heater and as a function of the at least one second temperature measured value.

15. A method in accordance with claim 14, further comprising:
providing an air inflow sensor in an air supply duct of the heater, wherein the air inflow sensor detects an air temperature of air flowing from the heater into the incubator chamber.

16. A method in accordance with claim 15, wherein the air inflow sensor is arranged in an area of discharge openings in fluid communication with the incubator chamber.

17. A method in accordance with claim 14, wherein the control device comprises electronics.

* * * * *